United States Patent [19]

Cooper

[11] Patent Number: 5,118,448
[45] Date of Patent: Jun. 2, 1992

[54] PROCESS FOR PRODUCING ESTERIFIED ALKOXYLATED POLYOLS

[75] Inventor: Charles F. Cooper, Paoli, Pa.

[73] Assignee: Arco Chemical Technology, L.P., Wilmington, Del.

[21] Appl. No.: 600,462

[22] Filed: Oct. 19, 1990

[51] Int. Cl.$^5$ ................................................. C11C 3/02
[52] U.S. Cl. ..................................... 554/168; 426/611;
568/613; 568/616; 568/618; 554/167; 554/170;
554/172; 554/173
[58] Field of Search .......................... 260/410.7, 410.6;
568/613, 676, 618; 426/611

[56] References Cited

U.S. PATENT DOCUMENTS

| | | | |
|---|---|---|---|
| 4,849,242 | 7/1989 | Kershner | 426/601 |
| 4,861,613 | 8/1989 | White et al. | 426/611 |
| 4,983,329 | 1/1991 | Cooper | 260/410.7 |

FOREIGN PATENT DOCUMENTS 035819 1/1990 European Pat. Off. .
207070 4/1982 German Democratic Rep. .

OTHER PUBLICATIONS

Sowden et al, Journal of the American Chemical Society, vol. 63, pp. 3244-3248, 1941.

Primary Examiner—Jose G. Dees
Assistant Examiner—Deborah D. Carr
Attorney, Agent, or Firm—Stephen D. Harper

[57] ABSTRACT

Esterified alkoxylated polyols useful as fat mimetics may be prepared by alkoxylating a benzylated polyol with an epoxide under basic conditions, reacting the benzyl ether group with hydrogen to convert it to a hydroxy group, and then esterifying with a fatty acid compound. The resulting product has at least one fatty acid ester group attached directly to the polyol residue.

20 Claims, No Drawings

PROCESS FOR PRODUCING ESTERIFIED ALKOXYLATED POLYOLS

FIELD OF THE INVENTION

This invention pertains to methods for the preparation of useful esterified alkoxylated polyols wherein at least one fatty acid ester group is connected directly to a polyol residue and at least one fatty acid ester group is connected to the polyol residue through a polyoxyalkylene segment.

BACKGROUND OF THE INVENTION

Esterified alkoxylated glycerin and other esterified alkoxylated polyols have recently been identified as useful reduced calorie fat substitutes. Compounds of this type, which are described more fully in U.S. Pat. No. 4,861,613, are substantially resistant to hydrolysis upon digestion owing to the high proportion of linkages in which the carbons adjacent to oxygen in the fatty acid ester groups are secondary or tertiary in structure. In a preferred embodiment of such substances, the structure may be represented as follows:

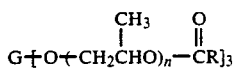

wherein G is a glyceryl radical, n is from about 1 to 3 on average, and R is a long chain paraffinic or olefinic hydrocarbon radical derived from a fatty acid.

However, the ability to use esterified alkoxylated polyols of this type at relatively high concentrations in food compositions is somewhat limited by the pronounced resistance of such substances to digestion. Since the esterified alkoxylated polyols are hydrolyzed and absorbed to only a very limited degree, they tend to retain their oil-like physical characteristics after ingestion. Consumption of large amounts of the fat substitutes can result in short bowel transit times and undesired laxative effects.

To enhance the acceptability of fat substitutes of this type, a modified esterified alkoxylated glycerin has been developed which is somewhat less resistant to enzymatic hydrolysis than previously known esterified alkoxylated glycerins and yet still has significantly reduced calorie availability as compared to a conventional fully digestible triglyceride lipid. This modified esterified alkoxylated glycerin has one fatty acid ester group attached directly to the end carbon of the glyceryl radical. Since this ester group is derived from a primary hydroxyl group, it is readily hydrolyzed upon ingestion, rendering the compound less fat-like in character owing to the loss of a long-chain fatty acid group.

The other two ester groups in the esterified alkoxylated glycerin are attached to the glyceryl radical through polyoxypropylene segments and thus are resistant towards enzymatic hydrolysis. The structure of a preferred embodiment of the esterified alkoxylated polyol is as follows:

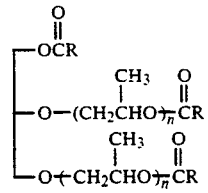

wherein R is a long-chain hydrocarbon radical derived from fatty acid.

The synthesis of such esterified alkoxylated monoglycerides is not straightforward. Esterified propoxylated glycerin may be prepared by reacting glycerin with propylene oxide in the presence of a basic alkali metal catalyst to form a propoxylated glycerin. The propoxylated glycerin is then esterified with a fatty acid compound such as a free fatty acid, fatty acid ester, or fatty acid halide. Using this synthetic approach, however, it is not possible to have an ester group attached directly to the glyceryl residue since the propylene oxide tends to add in a random fashion to all three hydroxyl groups of the starting glycerin:

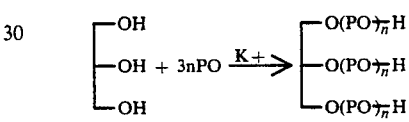

A possible alternative method of preparation of an esterified alkoxylated monoglyceride would be to propoxylate a fatty acid monoglyceride and then esterify the secondary hydroxyl groups of the propoxylated monoglyceride:

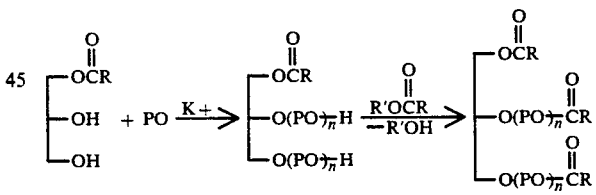

However, when this procedure is attempted, the product obtained is similar to the esterified propoxylated glycerin known in the prior art wherein oxypropylene units are present between the glyceryl radical and all three of the ester groups. Apparently, transesterification readily takes place under the reaction conditions necessary to achieve propoxylation of the fatty acid monoglyceride:

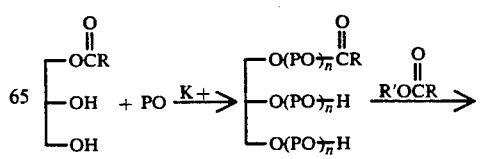

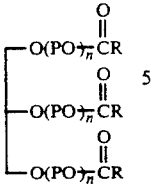

Thus, it is apparent there is a great need for processes whereby an esterified alkoxylated polyol having at least one ester group attached directly to the polyol residue may be readily prepared.

SUMMARY OF THE INVENTION

The process of this invention comprises the steps of a) reacting an epoxide and a benzylated polyol having at least one hydroxyl group and at least one benzyl ether group in the presence of an amount of a basic catalyst effective to react the epoxide with the hydroxyl group of the benzylated polyol to form an alkoxylated polyol benzyl ether, b) reacting the alkoxylated polyol benzyl ether and hydrogen in the presence of an effective amount of a transition metal hydrogenalysis catalyst to convert the benzyl ether group to an alcohol functionality to form alkoxylated polyol, and c) reacting the alkoxylated polyol with a fatty acid compound selected from the group consisting of free fatty acids, fatty acid esters, and fatty acid halides to form an esterified alkoxylated polyol having at least one ester group bonded directly to the polyol residue.

DETAILED DESCRIPTION OF THE INVENTION

In the first step of the process of this invention, a benzylated polyol and an epoxide are reacted in the presence of an amount of a basic catalyst effective to polymerize the epoxide.

The benzylated polyol starting material must have at least one hydroxyl group (preferably, an aliphatic hydroxyl group) and at least one benzyl ether group.

The benzyl ether group may be any functionality in which an aromatic ring and a divalent oxygen are bonded to the same carbon. Suitable benzyl ether groups may thus correspond to the structural formula

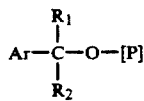

wherein Ar is the aromatic ring, P is the polyol residue, and $R_1$ and $R_2$ are the same or different and may be hydrogen, alkyl, aralkyl, or aryl. Alternatively, one of $R_1$ or $R_2$ may be an oxygen atom also bonded to P. Examples of suitable benzyl ether groups thus include

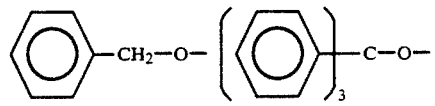

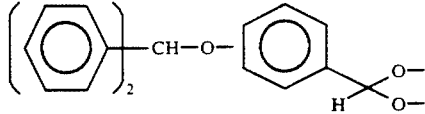

The polyol residue may be derived, for example, from a suitable diol, triol, tetrol, pentol, hexol, heptol, octol or other organic compound having more than two hydroxyl groups.

The benzylated polyol preferably has the general structure $[ArCH_2O]_xP[OH]_y$ wherein Ar is an aryl group such as phenyl, napthyl, phenanthryl, anthryl, or the like and P is the polyol residue. The aryl group may be unsubstituted or substituted with an alkyl, aryl, halo, alkoxy, nitro, cyano, or other such substituent. Preferably, however, Ar is phenyl. The benzyl group is most preferably connected to a primary aliphatic carbon in the polyol residue P (i.e., to a carbon bonded to one other carbon and two hydrogen atoms). The use of a benzylated polyol of this type will yield as esterified alkoxylated polyol wherein at least one ester group is bonded directly to a primary carbon in the polyol residue. This ester linkage will consequently be advantageously susceptible to enzymatic hydrolysis upon ingestion. The sum of x and y is preferably at least 3 and no greater than 8; x and y must each be at least 1.

Benzylated polyols suitable for use as the starting material in this process are well-known in the art and may be prepared by any appropriate method. For example, glycerin may be reacted with an aldehyde or ketone to form an acetal or ketal. The acetal or ketal is then reacted with alkali metal and a benzyl halide to obtain the mono-benzyl ether of the ketal or acetal. Hydrolysis in the presence of dilute acid yields the mono-benzyl ether of glycerin. Procedures of this type are described, for example, in Sowden et al., J. Am. Chem. Soc. 63, 3244(1941).

The preferred benzylated polyol is 3-phenylmethoxy-1,2-propanediol. This compound is commercially available from Biosynth International, Parish Chemical Co., Sigma Chemical Co., and Toronto Research Chemicals, Inc. and may also be prepared using the synthetic procedure described herein above.

Other suitable benzylated polyols include, but are not limited to:

a) mono-benzyl ethers of ethylene glycol, diethylene glycol, triethylene glycol, propylene glycol, dipropylene glycol, tripropylene glycol, 1,3-propanediol, 2-methyl-1,3-propanediol, 2,2-dimethyl-1,3-propanediol, 1,4-butanediol, 2,3-butanediol, 1,3-butanediol, 1,5-pentanediol, 1,6-hexanediol, pinacol, cyclohexane dimethanol, and isobutylene glycol;

b) mono- and di-benzyl ethers of glycerin, trimethylolpropane, trihydroxyhexane, trihydroxybutane, trihydroxybutane, trihydroxypentane, and erythrose;

c) mono-, di-, and tri-benzyl ethers of erythritol, pentaerythritol, threitol, ribose, arabinose, xylose, lyxose, and arabinose;

d) mono-, di-, tri-, and tetra-benzyl ethers of ribitol, arabitol, xylitol, allose, altrose, glucose, mannose, gulose, idose, galactose, talose, and fructose;;

e) mono-, di-, tri-, tetra-, and penta-benzyl ethers of dulcitol, iditol, mannitol, and sorbitol;

f) mono-, di-, tri-, tetra-, penta-, and hexa-benzyl ethers of perseitol; and g) mono-, di-, tri-, tetra-, penta-, hexa-, and hepta-benzyl ethers of sucrose, maltose, and lactose.

Examples of other benzylated polyols include 2-phenyl-1,3-dioxan-5-ol, 2-phenyl-1,3-dioxolane-4-methanol, 3-(triphenyl methoxy)-1,2-propanediol, 3(diphenyl methoxy)-1,2-propanediol, as well as benzyl ethers of polyols such as polyglycerol

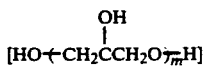

and polyvinyl alcohol

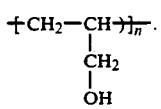

The benzylated polyol may be formed in situ during the alkoxylation step of this process. For example, benzyl alcohol may be reacted with an epoxide in the presence of a basic catalyst to form a mono-benzyl ether of an alkylene glycol which functions as the benzylated polyol in the subsequent alkoxylation.

The epoxide to be reacted in the alkoxylation step with the benzylated polyol may be any organic compound containing an oxiranyl functionality, but preferably is a $C_2$–$C_6$ aliphatic epoxide. Propylene oxide is the most preferred epoxide, but other suitable $C_2$–$C_6$ aliphatic epoxides include ethylene oxide, 1,2-butene oxide, isobutylene oxide, 2,3-butene oxide, 1,2-pentene oxide, 2,3-pentene oxide, cyclopentene oxide, 1,2-hexene oxide, cyclohexene oxide and the like. Other epoxides such as epichlorohydrin, 1-octene oxide, allyl glycidyl ether, phenyl glycidyl ether, phenyl glycidyl ether, styrene oxide, butadiene mono-oxide, and the like may also be used, however. Mixtures of epoxides may be employed. If more than one epoxide is used, it may be desirable to add the different epoxides sequentially so as to vary the location of the different oxyalkylene repeating units within the end product. It is particularly advantageous to introduce an oxyalkylene unit other than oxyethylene at the ends of the alkoxylated polyol benzyl ether since primary ester linkages in the final esterified alkoxylated polyol will be more susceptible to enzymatic hydrolysis than secondary or tertiary ester linkages.

The epoxide reacts with the hydroxyl group(s) of the benzylated polyol to form an alkoxylated polyol benzyl ether. Ring-opening of the epoxide occurs during this process. In a preferred embodiment of this invention, the alkoxylated polyol benzyl ether produced has the general structure

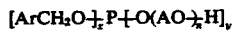

wherein Ar is an aryl radical, P is a polyol residue, AO is an oxyalkylene repeating unit derived from the epoxide, n is from about 1 to 25 on average, x and y are each at least 1, and the sum of x+y is an integer of from 3 to 8.

It has been found that the benzyl ether functionality of the benzylated polyol is inert under the alkoxylation conditions of this process. No oxyalkylene groups are inserted between the polyol radical and the benzyl ether group, in contrast to the transesterification and oxyalkylene insertion observed when an ester group is attached directly to the polyol.

The basic catalyst may preferably be selected from the group consisting of basic alkali metal compounds, basic alkaline earth compounds, and basic tertiary amines. Suitable alkali metal and alkaline earth catalysts include the hydrides, carbonates, oxides, hydroxides, carboxylates, alkoxides, and sulfates of lithium, sodium, potassium, barium, calcium, and strontium as well as the elemental forms of the metals (e.g., sodium or potassium metal dispersions). Generally speaking, it is desirable to pre-react the benzylated polyol with the alkali metal or alkaline earth catalyst to form the salt of the benzylated polyol prior to reaction with the epoxide. For example, if sodium hydroxide or potassium hydroxide is employed as the catalyst, a mixture of the benzylated polyol and catalyst may be heated under conditions such that the water formed by reaction of the components is removed and the alkali metal salt of the benzylated polyol is formed.

Suitable tertiary amines for use in this process include aliphatic, aromatic, and mixed aliphatic-aromatic amines such as triethylamine, N,N-dialkyl anilines, dimethylaminocyclohexane, tri-n-propylamine, tetraethyl ethylenediamine, N,N'-dialkylpiperazines, N-alkylpiperidines, pyridine and substituted pyridines, N-alkyl pyrrolidinones, quinuclidine, and the like.

The amount of basic catalyst employed must be sufficient to effectively catalyze the addition of the epoxide to the hydroxyl group(s) of the benzylated polyol. Preferably this amount is from about 0.01 to 1 equivalent of basic catalyst per equivalent of hydroxyl groups in the benzylated polyol. The epoxide and benzylated polyol are preferably reacted at a temperature of from about 50° C. to 175° C. for a time effective to accomplish substantial (e.g., over 25%) conversion of the epoxide. Reaction times of from 1 to 48 hours will typically suffice. The molar ratio of epoxide to benzylated polyol may be varied as desired depending upon the degree of alkoxylation desired in the final esterified alkoxylated polyol, but generally from about 1 to 25 equivalents of epoxide per equivalent of hydroxyl groups in the benzylated polyol will be typically employed. It is generally desirable to add the epoxide incrementally with agitation to the benzylated polyol and basic catalyst. The alkoxylation may be carried out in the presence of an inert organic solvent. When the desired degree of epoxide conversion has been achieved, the alkoxylated polyol benzyl ether may be purified by removing any unreacted epoxide by a suitable method such as vacuum stripping. The alkoxylated polyol benzyl ether may also be treated to remove the residual basic catalyst. Methods such as filtration, extraction, precipitation, or absorption can be used depending on the particular catalyst employed. Any of the standard methods for removing a basic catalyst from an alkoxylated product may be employed. If an alkali metal or alkaline earth catalyst is present, for example, a particularly advantageous method of catalyst removal involves heating the product with magnesium silicate to absorb the metal and then filtering to remove the magnesium silicate.

In the next step of the process, the alkoxylated polyol benzyl ether is reacted with hydrogen in the presence of an effective amount of a transition metal hydrogenalysis catalyst to form an alkoxylated polyol. In a preferred embodiment of the process, the resulting alkoxylated polyol has the general structure $[HO{\frac{}{x}}P{\frac{}{}}(O{\frac{}{}}AO)_{\overline{n}}H]_y$ wherein P, AO, x, y, and n have the same meaning as described hereinabove.

The benzyl ether groups of the alkoxylated polyol benzyl ether are converted to hydroxy groups. Surprisingly, however, no cleavage or decomposition of the ether linkages in the —O—(AO)—H segments of the alkoxylated polyol benzyl is observed under the reaction conditions of this invention. Another unexpected and beneficial result of the reaction of the alkoxylated polyol benzyl ether with hydrogen is the significant reduction in color which is achieved. Low color in the final product is highly desirable since it is to be used in the preparation of foodstuffs for human consumption.

While the temperature and amount of hydrogen employed are not critical, the reaction is preferably carried out at about 0.5 to 300 atmospheres hydrogen pressure at a temperature of from about 0 to 300° C. When a relatively active transition metal hydrogenolysis catalyst is employed, the hydrogen pressure need only be from about 1 to 10 atmospheres. Reaction temperatures of from about 50° C. to 175° C. are normally sufficient. Reaction with hydrogen is continued until substantially all (i.e., over 95%) of the benzylether groups have been converted to hydroxyl groups. Typically, this will require from 2 to 72 hours.

Higher hydrogen pressures (50-300 atmospheres) and reaction temperatures (75° C. to 300° C.) are generally desirable if a less active hydrogenolysis catalyst is selected. The transition metal of the transition metal hydrogenolysis catalyst is preferably selected from the group consisting of palladium, nickel, platinum, rhodium, ruthenium, zinc, cobalt, copper, chromium and combinations thereof. Of these metals, nickel, rhodium, platinum, and, especially, palladium are preferred for use. Particularly advantageous catalysts include, for example, finely divided metallic platinum, palladium on charcoal, platinum black, platinum sponge, Raney nickel, palladium hydroxide on carbon, palladium black, palladium on activated carbon, palladium on alumina, palladium on barium carbonate, palladium on barium sulfate, palladium on calcium carbonate, palladium-poly(ethylenimine) on silica gel, palladium oxide, palladium sponge, rhodium on alumina, colloidal palladium, and the like. The transition metal may be supported on an inert support such as carbon, alumina, barium sulfate, calcium carbonate, or strontium carbonate. The amount of the transition metal catalyst should be sufficient to effect substantial conversion of the benzyl groups to hydroxyl groups. Typically, from about 0.001 to 10 weight percent of transition metal catalyst based on the weight of the alkoxylated polyol benzyl ether will suffice. The hydrogenation may be carried out in a solvent; aliphatic alcohols and other polar organic solvents are particularly preferred for this purpose.

The alkoxylated polyol thus obtained is then esterified by reacting with a fatty acid compound selected from the group consisting of free fatty acids, fatty acid esters, and fatty acid halides. The esterification yields an esterified alkoxylated polyol having at least one ester group bonded directly to the polyol residue.

In a preferred embodiment of the invention, the esterified alkoxylated polyol has the general structure

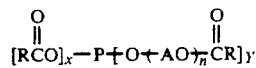

wherein P, AO, x, y, and n have the same meaning as described hereinabove and R is a hydrocarbon radical derived from the fatty acid compound.

The fatty acid compound may preferably be a fatty acid or fatty acid ester having the general structure $$\underset{R'OCR}{\overset{O}{\|}}$$

wherein R is a $C_{11}$–$C_{23}$ olefinic or paraffinic hydrocarbon radical and R' is hydrogen or a $C_1$–$C_6$ hydrocarbon radical. Examples of suitable fatty acids include, but are not limited to, caprylic, capric, lauric, myristic, myristoleic, stearic, palmitic, palmitoleic, rincinoleic, linoleic, linolenic, elaeostearic, arachidic, arachidonic, behenic, erucic, oleic, and heptadeconoic acid. The fatty acids may be derived synthetically or from natural sources such as triglyceride lipids. Exemplary fatty acid esters include the methyl, ethyl, propyl, and isopropyl esters of the foregoing fatty acids.

Fatty acid halides which may be used in the process of this invention can have the general structure $$\underset{XCR}{\overset{O}{\|}}$$

wherein R is a $C_{11}$–$C_{23}$ olefinic or paraffinic hydrocarbon radical and X is halide, preferably chloride or bromide. Mixtures of fatty acid compounds, such as the mixtures of fatty acids typically obtained by hydrolysis of a triglyceride such as corn oil or soybean oil, may be used.

The alkoxylated polyol and the fatty acid compound are reacted for a time and at a temperature sufficient to accomplish substantially complete (i.e., greater than 90%) esterification of the hydroxyl groups of the alkoxylated polyol. The optimum reaction conditions will vary somewhat depending upon the particular type of fatty acid compound used. If a fatty acid or fatty acid ester is utilized, the reaction temperature is preferably from about 100° C. to 350° C; reaction times of from about 1 to 48 hours are generally sufficient to accomplish substantially complete esterification of the hydroxyl groups. A co-product having the structure HOR, will be generated as the esterification proceeds. To drive the reaction to completion, it is desirable to remove the co-product from the reaction mixture as it forms by a suitable method such as distillation or vacuum stripping. A catalyst may be employed if desired to shorten the reaction time required. If the fatty acid moiety is a free fatty acid, the catalyst is preferably an acidic catalyst. If a fatty acid ester is used, an acidic or basic catalyst may be present during esterification. When the fatty acid moiety is a fatty acid halide, somewhat lower reaction temperatures (e.g., about 25° C. to 125° C.) are sufficient, particularly if a tertiary amine such as triethylamine is additionally present to take up the HX generated during the esterification reaction.

Reaction times of from about 1 to 48 hours are typically sufficient.

To accomplish substantially complete esterification of the alkoxylated glyceride, at least about 1 (more preferably, at least about 1.1) equivalent of the fatty acid compound per equivalent of hydroxyl groups in the alkoxylated polyol are used. For reasons of economy, it is preferred to react not more than about 3 equivalents of fatty acid compound. Any excess fatty acid compound may be removed from the esterified alkoxylated polyol product by an appropriate method such as vacuum steam stripping.

Without further elaboration, it is believed that one skilled in the art can, using the preceding description, utilize the present invention to its fullest extent. The following examples, therefore, are to be considered as merely illustrative and not limitative of the claims or remainder of the disclosure in any way whatsoever.

EXAMPLE 1

Step 1—Preparation of Alkoxylated Glycerin Benzyl Ether

3-Phenylmethoxy-1,2-propanediol (181 parts) was mixed with 30% aqueous potassium hydroxide (7.4 parts) and toluene (150 parts). The mixture was heated to reflux and water removed as an azeotrope with toluene. The product obtained was added to a stirred pressure reactor and heated to 100° C. Propylene oxide (460 parts) was added incrementally, keeping the reaction temperature below 110° C. When addition was completed, the mixture was heated for several more hours at 100-110° C. to react substantially all of the propylene oxide. After purging with nitrogen, magnesium silicate (10% weight) was added and the mixture heated 2 hrs. at 90° C. to remove the residual potassium catalyst. The alkoxylated polyol benzyl ether product obtained after filtration was a clear liquid having the following structure:

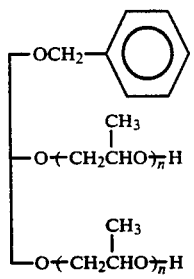

wherein n was approximately 4.

Step 2—Preparation of Alkoxylated Glycerin

The alkoxylated polyol benzyl ether prepared in Step 1 (550 parts) was added to a pressure reactor equipped with a stirrer. After purging with nitrogen, ethanol (300 parts) and palladium black (2 parts) were added and hydrogen introduced until the hydrogen pressure was 100 psi (6.8 atm). After heating to 100° C, the hydrogen pressure was increased to 300 psi (20.4 atm) and maintained at that pressure for 24 hours. The reactor was then purged with nitrogen and the catalyst removed by filtration. The alkoxylated polyol product obtained after removal of the ethanol and other volatiles by vacuum stripping was a colorless liquid. No residual benzyl groups were detectable by $^1$H or $^{13}$C NMR; the structure of the product was thus confirmed as

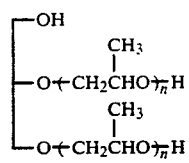

wherein n was approximately 4.

Step 3—Preparation of Esterified Alkoxylated Glycerin

The alkoxylated polyol from Step 2 (98 parts) was mixed with soybean fatty acids (208 parts) and heated to 240° C. The reaction was monitored by isocratic liquid chromatography using a silica gel column and ethyl acetate as the eluant. When over 95% conversion of the hydroxyl groups was achieved, the excess fatty acid was removed by vacuum steam distillation at 240° C. (1 mm Hg pressure). The esterified alkoxylated polyol product obtained was a light yellow clear oil having the odor, appearance, and taste of refined soybean oil. The structure of the product was determined to be:

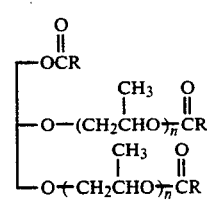

wherein n was approximately 4 on average and R was a $C_{15}$-$C_{17}$ olefinic or paraffinic hydrocarbon radical derived from the soybean fatty acids.

EXAMPLE 2

Step 1—Preparation of Alkoxylated Threitol Mono-benzyl Ether 4-(Phenylmethoxyl)-1,2,3-butanetriol (212 parts) is mixed with 25 weight % sodium methoxide in methanol (43.2 parts) and heated at approximately 70° C. until methanol evolution ceases. The mixture is then heated at 50° C. under vacuum (1 mm Hg) to remove any remaining methanol, forming the sodium salt of the 4-(phenylmethoxyl)-1,2,3-butanetriol. The product obtained is added to a stirred pressure reactor and heated to 100° C. A mixture of ethylene oxide (264 parts) and propylene oxide (1392 parts) is then added incrementally, keeping the reaction temperature below 110° C. When addition is complete, the mixture is heated for several more hours at 100-110° C. to react substantially all of the epoxide. After purging with nitrogen, magnesium silicate (3% by weight) is added and the mixture heated 1 hour at 110° C. to remove the residual sodium catalyst. The alkoxylated threitol mono-benzyl ether product obtained after filtration of the magnesium silicate is a liquid having the following structure:

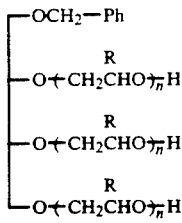

wherein R is hydrogen or methyl and n is approximately 10. The molar ratio of oxyethylene to oxypropylene repeating units is approximately 1:4.

Step 2—Preparation of Alkoxylated Threitol

The alkoxylated threitol mono-benzyl ether prepared in Step 1 (1868 parts) is added to a pressure reactor equipped with a stirrer. After purging with nitrogen, isopropyl alcohol (1000 parts) and Raney nickel (90 parts) are added and hydrogen introduced until the hydrogen pressure reached 25 atmospheres. After heating to 150° C., the hydrogen pressure is increased to 175 atmospheres and maintained at that pressure for 20 hours. The alkoxylated threitol product obtained after filtration and removal of the isopropyl alcohol and other volatiles has the structure

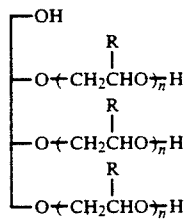

wherein n is approximately 10 on average and R is either hydrogen or methyl.

Step 3—Preparation of Esterified Alkoxylated Threitol

The alkoxylated threitol from Step 2 (1766 parts) is mixed with methyl oleate (890 parts) and potassium methoxide (transesterification catalyst; 15.5 parts). The mixture is heated at 150° C. for 3 hours under vacuum (10 mm Hg) to continuously remove the methanol which is generated. The residual potassium is removed by heating with magnesium silicate (50 parts) for 2 hours at 100° C. and then filtering. Excess fatty acid ester is removed by vacuum steam stripping, yielding an esterified alkoxylated threitol having the structure

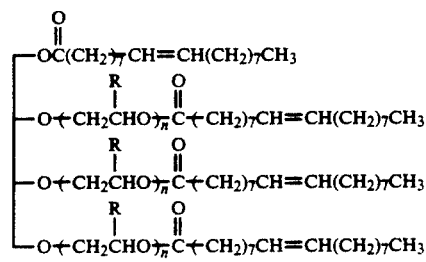

wherein n is about 10 on average and the molar ratio of oxyethylene to oxypropylene repeating units is about 1:4.

EXAMPLE 3

Step 1—Preparation of Alkoxylated Glycerin Di-Benzyl Ether 2,3-Bis(phenylmethoxy)-1-propanol (272 parts) is mixed with dimethylaminocyclohexane (4.5 parts) and 1,2-butene oxide (576 parts) and heated to 125° C. in a stirred pressure reactor. The mixture is allowed to react at 125° C. until approximately 2 equivalents of 1,2-butene oxide have reacted with the 2,3-bis(phenylmethoxy)-1-propanol. Unreacted 1,2-butene oxide and residual tertiary amine catalyst are removed under vacuum to yield an alkoxylated glycerin di-benzyl ether having the structure

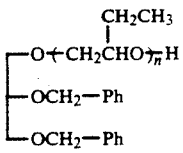

wherein n is approximately 2 on average.

Step 2—Preparation of Alkoxylated Glycerin

The alkoxylated glycerin di-benzyl ether prepared in Step 1 (344 parts) is added to a pressure reactor equipped with a stirrer. After purging with nitrogen, platinum on alumina (5% Pt; 325 mesh powder; 20 parts) is added. The mixture is heated at 75° C. for 18 hours while maintaining a constant hydrogen pressure of 50 atmospheres. The reactor is cooled, purged with nitrogen, and the catalyst removed by filtration. The alkoxylated glycerin product obtained after stripping under vacuum has the structure

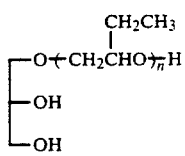

wherein n is about 2 on average.

Step 3—Preparation of Esterified Alkoxylated Glycerin

A solution of a 1:5 molar ratio of palmitoyl chloride (104 parts) and oleoyl chloride (578 parts) in dry chloroform (500 parts) is added slowly to a stirred solution of the alkoxylated glycerin from Step 2 (164 parts) in dry chloroform (300 parts) and dry pyridine (182 parts). The addition is made at room temperature under an atmosphere of dry nitrogen. After stirring for an additional 24 hours, the mixture is added to water (2000 parts) and then extracted three times with petroleum ether (3×1000 parts). The combined organic layers are washed with water (2×1000 parts), dilute, aqueous HCl (2×1000 parts), water (2×1000 parts), aqueous potassium bicarbonate (2×1000 parts), and then water (2×1000 parts). The organic layer is dried over sodium sulfate and the solvent removed by vacuum stripping. To remove any remaining fatty acid, the product is heated to between 200–205° C. under vacuum (10 mm Hg) and water slowly bled under the surface of the liquid. The total amount of water thus introduced is about 3 parts water per part esterified alkoxylated glycerin. The structure of the final product is as follows:

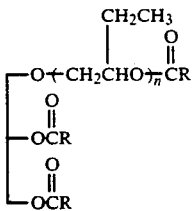

wherein n is about 2 on average and R is either —(CH₂)₇CH=CH(CH₂)₇CH₃ or —(CH₂)₁₄CH₃, the molar ratio of the two types of R groups being approximately 5:1.

COMPARATIVE EXAMPLE 4

This example demonstrates the difficulties associated with the use of a monoglyceride as the starting material in the preparation of an esterified alkoxylated polyol having at least one ester group attached directly to the polyol radical.

Safflower monoglyceride (352 parts) was mixed with potassium hydroxide (2 parts) and the mixture heated at 110° C. under vacuum to remove the water generated. Propylene oxide (464 parts) was added on a pressure demand basis at 90–100° C. After treating with magnesium silicate to remove the potassium catalyst, the product obtained had the structure:

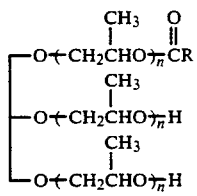

The structure was verified by heating the product in refluxing methanol in the presence of a catalytic amount of sodium methoxide to cleave any ester groups present. No primary glycerol hydroxyl groups were detectable in the reacted product by ¹³C NMR analysis, indicating that transesterification had occurred during alkoxylation resulting in insertion of oxypropylene repeating units between the glyceryl residue and the ester group originally attached directly to the glyceryl residue in the safflower monoglyceride. This method therefore is not suitable for the preparation of an esterified alkoxylated glycerin having at least one ester group attached directly to the glyceryl radical.

I claim:

1. A process for producing an esterified alkoxylated polyol having at least one fatty acid ester group bonded directly to a polyol residue, said process comprising the steps of
   (a) reacting an epoxide and a benzylated polyol having at least one hydroxyl group and at least one benzyl ether group in the presence of an amount of a basic catalyst effective to react the epoxide with the hydroxyl group of the benzylated polyol to form an alkoxylated polyol benzyl ether;
   (b) reacting the alkoxylated polyol benzyl ether and hydrogen in the presence of an effective amount of a transition metal hydrogenolysis catalyst to convert the benzyl ether group to an alcohol functionality to form an alkoxylated polyol; and
   (c) reacting the alkoxylated polyol with a fatty acid compound selected from the group consisting of free fatty acids, fatty acid esters, and fatty acid halides to form the esterified alkoxylated polyol.

2. The process of claim 1 wherein the benzylated polyol has the structure

wherein Ar is an aryl group, x and y are the same or different and are integers of from 1 to 7, the sum of x and y is from 2 to 8, and Polyol is the polyol residue.

3. The process of claim 1 wherein said epoxide is a C₂–C₆ aliphatic epoxide.

4. The process of claim 1 wherein the transition metal of the transition metal hydrogenolysis catalyst is selected from the group consisting of palladium, nickel, platinum, and rhodium.

5. The process of claim 1 wherein the fatty acid compound is a fatty acid ester.

6. The process of claim 1 wherein the fatty acid compound is a free fatty acid.

7. A process for producing an esterified alkoxylated polyol having at least one fatty acid ester group bonded directly to a polyol residue comprising the steps of
   (a) reacting at C₂–C₆ aliphatic epoxide and a benzylated polyol having the structure

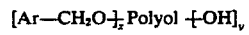

wherein Ar is a aryl group, Polyol is the polyol residue, x and y are the same or different and are integers of from 1 to 7, and the sum of x+y is an integer of from 3 to 8, in the presence of an amount of a basic catalyst selected from the group consisting of alkali metal compounds, alkaline earth compounds, and tertiary amines effective to react the epoxide to form an alkoxylated polyol benzyl ether of structure

wherein AO is an oxyalkylene repeating unit and n is from about 1 to 25 on average;
   (b) reacting the alkoxylated polyol benzyl ether and hydrogen in the presence of an effective amount of a transition metal hydrogenolysis catalyst wherein the transition metal is palladium, platinum, nickel, or rhodium to form an alkoxylated polyol of structure

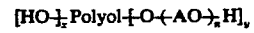

and;
   (c) reacting the alkoxylated polyol with a fatty acid compound selected from the group consisting of free fatty acids, fatty acid esters, and fatty acid halides to form an esterified alkoxylated polyol having the structure

wherein R is a hydrocarbon radical derived from the fatty acid moiety.

8. The process of claim 7 wherein the C₂–C₆ aliphatic epoxide is selected from the group consisting of ethylene oxide, propylene oxide, 1,2-butene oxide, and mixtures thereof.

9. The process of claim 7 wherein the sum of x+y is 3.

10. The process of claim 7 wherein the fatty acid compound is a $C_{12}$-$C_{24}$ free fatty acid or a mixture of $C_{12}$-$C_{24}$ free fatty acids.

11. The process of claim 7 wherein the fatty acid compound is a $C_1$-$C_6$ alkyl ester of a $C_{12}$-$C_{24}$ fatty acid or a mixture of $C_1$-$C_6$ alkyl ester of $C_{12}$-$C_{24}$ fatty acids.

12. The process of claim 7 wherein the basic catalyst is an alkali metal compound wherein the alkali metal is sodium or potassium.

13. The process of claim 7 wherein at least one ArCH$_2$O— group of the benzylated polyol is bonded to a primary carbon of the polyol residue.

14. A process for producing an esterified alkoxylated glycerin having at least one fatty acid ester group bonded directly to a glyceryl residue, said process comprising the steps of
   (a) reacting an epoxide selected from the group consisting of ethylene oxide, propylene oxide, and 1,2-butene oxide and a benzylated glycerin having the structure

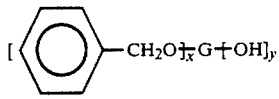

wherein G is the glyceryl residue, x is 1 or 2, y is 1 or 2, and the sum of x+y is 3 in the presence of an amount of a basic alkali metal compound effective to react the epoxide to form an alkoxylated glycerin benzyl ether of structure

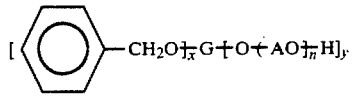

wherein AO is an oxyalkylene repeating unit having from 2 to 4 carbons and n is from about 1 to 25 on average;

(b) reacting the alkoxylated glycerin benzyl ether and hydrogen in the presence of an effective amount of a transition metal hydrogenolysis catalyst wherein the transition metal is selected from the group consisting of palladium, platinum, nickel, and rhodium to form an alkoxylated glycerin of structure

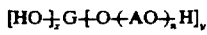

and;

(c) reacting the alkoxylated glycerin with a fatty acid compound having the structure

wherein R is a $C_{11}$-$C_{23}$ olefinic or paraffinic hydrocarbon radical and R' is hydrogen or a $C_1$-$C_6$ hydrocarbon radical to form an esterified alkoxylated glycerin having the structure

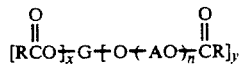

15. The process of claim 14 wherein x is 1 and y is 2.

16. The process of claim 14 wherein step (a) is carried out at a reaction temperature of from about 50° C. to 175° C.

17. The process of claim 14 wherein the amount of basic alkali metal catalyst is from about 0.01 to 1 equivalent per equivalent of y in the benzylated polyol.

18. The process of claim 14 wherein step (b) is carried out at about 1 to 300 atmospheres hydrogen pressure and a temperature of from about 50° C. to 300° C.

19. The process of claim 14 wherein step (c) is carried out at a temperature of from about 100° C. to 350° C.

20. The process of claim 14 wherein the epoxide is propylene oxide.

* * * * *